US012758114B2

(12) United States Patent
Cadore Mafaldo et al.

(10) Patent No.: US 12,758,114 B2
(45) Date of Patent: Oct. 13, 2026

(54) NON-INVASIVE METHOD FOR ANALYZING LIQUID IMPLANTS IN DEEP ANATOMICAL PLANES

(71) Applicants: Rodrigo Cadore Mafaldo, Porto Alegre (BR); Danuza Dias Mafaldo, Porto Alegre (BR); Elenilson De Godoy Alves Filho, Fortaleza (BR); Lorena Mara Alexandre E Silva, Fortaleza (BR)

(72) Inventors: Rodrigo Cadore Mafaldo, Porto Alegre (BR); Danuza Dias Mafaldo, Porto Alegre (BR); Elenilson De Godoy Alves Filho, Fortaleza (BR); Lorena Mara Alexandre E Silva, Fortaleza (BR)

( * ) Notice: Subject to any disclaimer, the term of this patent is extended or adjusted under 35 U.S.C. 154(b) by 165 days.

(21) Appl. No.: 18/654,536

(22) Filed: May 3, 2024

(65) Prior Publication Data

US 2024/0277249 A1 Aug. 22, 2024

Related U.S. Application Data

(63) Continuation of application No. PCT/BR2022/050496, filed on Dec. 13, 2022.

(30) Foreign Application Priority Data

Dec. 22, 2021 (BR) .......................... 1020210260599

(51) Int. Cl.
*A61B 5/055* (2006.01)

(52) U.S. Cl.
CPC .................................... *A61B 5/055* (2013.01)

(58) Field of Classification Search
CPC ......... A61B 5/055; G01R 33/46; G01N 24/08
USPC .......................................................... 324/308
See application file for complete search history.

(56) References Cited

U.S. PATENT DOCUMENTS

| | | | | |
|---|---|---|---|---|
| 8,779,770 | B2 | 7/2014 | Butts et al. | |
| 10,401,312 | B2 * | 9/2019 | Takis | G01N 24/08 |
| 2009/0192725 | A1 * | 7/2009 | Markley | G01R 33/465 324/307 |
| 2010/0315083 | A1 | 12/2010 | Pauli et al. | |
| 2020/0033430 | A1 | 1/2020 | Mariano et al. | |
| 2025/0017769 | A1 * | 1/2025 | DiLeo | A61L 27/54 |

FOREIGN PATENT DOCUMENTS

CN 108445034 A 8/2018

OTHER PUBLICATIONS

PCT/BR2022/050496 ; Filiing Date: Dec. 13, 2022, Includes ISR, Written Opinion.
Barekatain, Y. et al., “Robust detection of oncometabolic aberrations by 1H—13C heteronuclear single quantum correlation in intact biological specimens”, Communications Biology, 3(1):328, Jun. 25, 2020, 11 pages.
Dufour, G. et al., “2D-Cosy NMR Spectroscopy as a Quantitative Tool in Biological Matrix: Application to Cyclodextrins”, The AAPS Journal, 17(6), pp. 1501-1510, Aug. 25, 2015.
Wang, Y. et al., “Unequivocal identification of two-bond heteronuclear correlations in natural products at nanomole scale by i-HMBC”, Nature Communications, 14:1842, Apr. 3, 2023, 11 pages.

* cited by examiner

*Primary Examiner* — Roberto Velez
(74) *Attorney, Agent, or Firm* — Rosenthal IP Law; Lawrence Rosenthal

(57) ABSTRACT

A non-invasive method for analyzing liquid implants in the deep anatomical planes of humans is described, which uses magnetic resonance imaging (MRI) spectroscopy combined with nuclear magnetic resonance (NMR) spectroscopy to obtain data on the structure and properties of the implanted material, making it possible to identify its origin, type and quantity in order to speed up interventions in the event of adverse events, or even for analysis and diagnostic purposes.

2 Claims, No Drawings

NON-INVASIVE METHOD FOR ANALYZING LIQUID IMPLANTS IN DEEP ANATOMICAL PLANES

CROSS-REFERENCE TO RELATED APPLICATIONS

This application is a CONTINUATION application claiming the benefit of priority of the co-pending the International Patent Application No. PCT/BR2022/050496 with an international filing date 13 Dec. 2022 that designated the United States, which claims the benefit of priority of Federal Republic of Brazil Application No. 1020210260599, filed 22 Dec. 2021, the entire disclosures of each (and all) of which applications are expressly incorporated by reference in their entirety herein.

FIELD OF THE INVENTION

The present invention patent describes a non-invasive method for analyzing liquid implants in deep anatomical planes of humans, which uses magnetic resonance imaging (MRI) spectroscopy combined with nuclear magnetic resonance (NMR) spectroscopy to obtain data on the structure and properties of the implanted material, making it possible to identify origin, type and quantity in order to speed up interventions, in case of adverse actions, or even for analysis and diagnostic purposes.

BACKGROUND OF THE INVENTION

Liquid implants are characterized by being biocompatible materials implanted in the human body via microcannulas, widely used in aesthetic procedures, but also in procedures for facial and body volumetric correction, such as lipodystrophy.

These injectable fillers are an increasingly popular alternative to incisional cosmetic surgery and can be classified as temporary or permanent. Hyaluronic acid (HA) is commonly administered as a temporary filler that slowly disappears through enzymatic degradation. Permanent fillers include hydroxyapatite (Radiesse, Merz, Raleigh, NC) and polymethylmethacrylate (PMMA), among others (Broder K W, Cohen S R. An overview of permanent and semi-permanent fillers. Plast Reconstr Surg. 2006; 118 (3 Suppl): 7s-14s; Zielke H, Wolber L, Wiest L, Rzany B. Perfis de risco de diferentes preenchimentos injetáveis: resultados do Estudo de Segurança do Enchimento Injetável (Risk profiles of different injectable fillers: results of the Injectable Filler Safety Study)(IfS Study). Dermatol Surg. 2008; 343: 326-335.).

In the case of hyaluronic acid, in small quantities, there is a low incidence of serious complications (Rzany B, Cartier H, Kestermont P et al. Correction of tear troughs and periorbital lines with a range of customized hyaluronic acid fillers. J Drugs Dermatol. 2012; 11 (1 Suppl): s27-s34). A major benefit of HA is that it can be easily dissolved with hyaluronidase if there is an unwanted or adverse effect. The duration of action is 6 months with a residual effect of up to 2 to 3 years.

In the case of PMMA, the literature reports, for example, its use in healthcare since 1936, as a dental prosthesis, and as a soft tissue filler since 1988. In 1993, solid PMMA microspheres were mixed with bovine collagen so that the product could be implanted by needle without surgery.

PMMA is a permanent, biocompatible, non-toxic, non-sensitizing and non-migratory material (Carvalho Costa I M, Salaro C P, Costa M C. Polymethylmethacrylate facial implant: a successful personal experience in Brazil for more than 9 years. Dermatol Surg. 2009; 358: 1221-1227.), and its application promotes volume and an improvement in skin quality, unlike hyaluronic acid which promotes a volumetric increase, but without significant tissue stimulation. PMMA injections have been associated with undesirable effects on the eyelids and periocular region. A giant granulomatous cell reaction can occur with phagocytosis of PMMA particles, hardening of local tissues, edema, erythema and nodule formation in facial fillers, developing into a late-type inflammatory reaction six months after the PMMA injection. (Roberto Murillo Limongi, MD, Jeremiah Tao, MD, André Borba, MD, Filipe Pereira, MD, Ana Rosa Pimentel, MD, Patrícia Akaishi, MD, Antônio Augusto Velasco e Cruz, MD, PHD, Complications and Management of Polymethylmethacrylate (PMMA) Injections to the Midface, Aesthetic Surgery Journal, Volume 36, Issue 2, February 2016, Pages 132-135, https://doi.org/10.1093/asj/sjv195).

Because it is a liquid implant injected into deep layers of the skin, and its total removal is exceedingly difficult and complicated, PMMA is considered a permanent implant (JUNKINS-HOPKINS, J. M. Filler complications. J Am Acad Dermatol., v. 63, n. 4, p. 703-5, 2015.). Regardless of the amount applied, chronic inflammatory reactions, chronic pain, infections, nodule formation, stiffening of the area, rejection by the body and even tissue necrosis can occur, and the risk increases with the amount applied. When applied in large volumes, PMMA can spread to other areas of the body (PAPAZIAN, Marta Fernandes et al. Main aspects of facial fillers. Revista Faipe, v. 8, n. 1, p. 101-116, 2018.).

In order to verify the origin of the liquid implant, the type and quantity applied in deep anatomical planes, an incision is required at the application site, which, depending on the area, leads to aesthetic problems. However, in a number of situations, usually when adverse reactions occur in the body, it is necessary to identify the material applied in order to intervene properly and avoid major and irreversible tissue damage. For instance, the origin of the liquid implant can be obtained from its optical markers and based on this information, the origin and composition of the implant can be verified.

As surgical incision is a drastic action, less invasive procedures are usually conducted, such as reaction with enzymatic agents (e.g., hyaluronidase) or the administration of corticosteroids or other anti-inflammatory treatments.

The state of the art describes a method for investigating the biological compatibility of synthetic materials for medical and biological purposes with biological tissues. Document RU2007117420 describes the analysis of the implant using microscopy, with the production of a surface image with a resolution of nanometers. At the same time, the cut of the implant is investigated by atomic force microscopy methods, and the investigation of the cut implant by atomic force microscopy method is conducted in two contact modes: constant force and lateral forces. The images recorded in constant force mode, roughness parameters and height difference are calculated, so that the lateral force recording mode makes it possible to differentiate scanning areas with various coefficients of friction, and also peculiarities of the implant surface relief. The atomic force spectroscopy method is used to record adhesion forces between probe and implant surface and the measurement of adhesion force to assess the extent of penetration of connective tissue components and the extent of implant fixation in the body.

However, the state of the art does not describe or suggest a non-invasive method for analyzing liquid implants in deep anatomical planes that uses magnetic resonance imaging (MRI) spectroscopy combined with nuclear magnetic resonance (NMR) spectroscopy to obtain data on the structure and properties of the implanted material, making it possible to identify origin, type and quantity in order to speed up interventions in the event of adverse actions, or even for analysis and diagnostic purposes.

Although NMR spectroscopy is used to assess pathological processes in human tissues, particularly myopathies and myocardiopathies and metabolites in the brain, the relatively low sensitivity of NMR detects only a few of the numerous chemical components, generally those present in concentrations above 0.5 mMol.

Thus, the subject of this patent is a non-invasive method for analyzing liquid implants in deep anatomical planes in which the images and 1H atom NMR spectra corresponding to the areas analyzed make it possible to define the percentages of the compounds present in the samples based on the values of the integrations of the respective signals.

The non-invasive method for analyzing liquid implants in deep anatomical planes comprises, in a first step, mixing about 100 mg of the PMMA sample with about 600 pL of deuterated chloroform (CDCh), followed by filtration, with the resulting solution being added to the NMR tube (5 mm).

The NMR spectra are acquired with an accumulation of eight scans, under quantitative conditions (calibrated pulse, controlled temperature, and acquisition and waiting times between acquisitions sufficient for complete relaxation of the nuclei).

After acquiring the spectra, the quantification of the compounds present in the sample is obtained using an external standard, i.e., the values of the signal integrals of the target compounds are directly compared to the value of the signal integral and a certified standard (sucrose 99.9%, Sigma-Aldrich) used in the analysis.

The compounds are elucidated by NMR by identifying the chemical shifts and integral values acquired in the 1H NMR spectra, correlations between the 1H atoms acquired in the COSY (Correlation Spectroscopy) spectra, correlation to a bond between the 1H and carbon 13 (13C) atoms acquired in the HSQC (Heteronuclear Single Quantum Coherence) spectra, and correlation to more than one bond between the 1H and 13C atoms acquired in the HMBC (Heteronuclear Multiple Bond Correlation) spectra.

What is claimed is:

1. A non-invasive method for an analysis of liquid implants in deep anatomical planes comprising the following steps:

a) mixing about 100 mg to a polymethylmethacrylate (PMMA) sample with about 600 μl of deuterated chloroform (CDCl3), followed by filtration, to form a solution;

b) adding the solution to a nuclear magnetic resonance (NMR) tube;

c) acquiring NMR spectra of the solution using an accumulation of eight scans;

d) comparing values of signal integrals of target compounds to a value of a signal integral obtained from the solution and from a sucrose 99.9% certified standard used in the analyses;

e) identify chemical shifts and values of integrals acquired in hydrogen 1 (1H) NMR spectra, correlations between 1H atoms acquired in a Correlation Spectroscopy (COSY) spectra, correlation to a bond between the 1H and carbon 13 (13C) atoms acquired in Heteronuclear Single Quantum Coherence (HSQC) spectra, and correlation to more than one bond between the 1H and 13C atoms acquired in a Heteronuclear Multiple Bond Correlation (HMBC) spectra, to obtain information related to structure and properties of the liquid implants.

2. The method according to claim 1, characterized in that the NMR spectra are acquired under quantitative conditions comprising calibrated pulse, controlled temperature, and acquisition and waiting times between acquisitions sufficient for complete relaxation of a nuclei.

* * * * *